Figure 1:
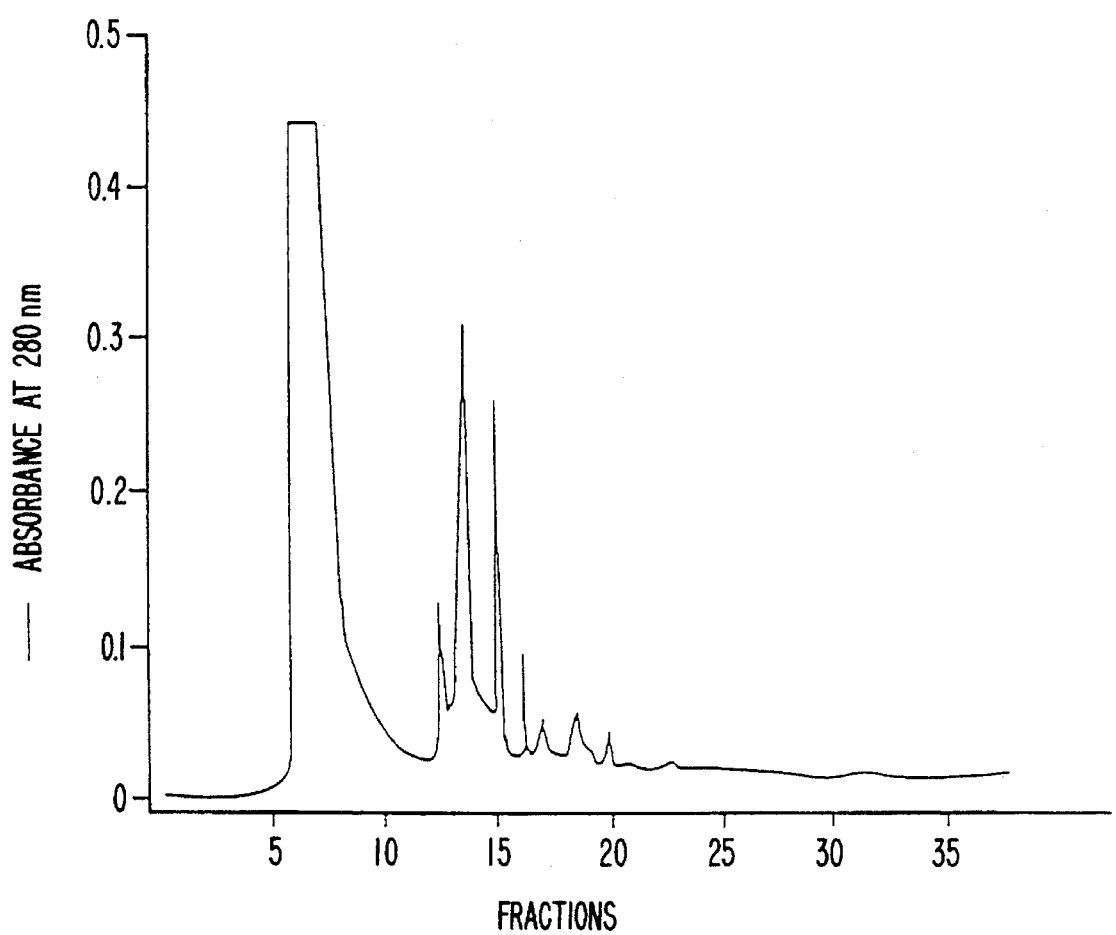

US005529792A

United States Patent [19]
Risau et al.

[11] Patent Number: 5,529,792
[45] Date of Patent: Jun. 25, 1996

[54] INHIBITORS OF ENDOTHELIAL CELL PROLIFERATION

[75] Inventors: Werner Risau, Gräfelfing; Hannes Drexler, München, both of Germany

[73] Assignee: Max-Planck-Gesellschaft zur Förderung der Wissenschaften e.V., Göttingen, Germany

[21] Appl. No.: 108,573

[22] PCT Filed: Feb. 27, 1992

[86] PCT No.: PCT/EP92/00419

§ 371 Date: Nov. 10, 1993

§ 102(e) Date: Nov. 10, 1993

[87] PCT Pub. No.: WO92/15606

PCT Pub. Date: Sep. 17, 1992

[30] Foreign Application Priority Data

Mar. 1, 1991 [DE] Germany .......................... 41 06 570.0

[51] Int. Cl.$^6$ .................................................. A61K 35/30
[52] U.S. Cl. .......................... 424/570; 424/520; 424/582; 514/2; 514/21
[58] Field of Search ...................................... 424/520, 570, 424/582; 514/2, 21

[56] References Cited

FOREIGN PATENT DOCUMENTS 0312246 4/1989 European Pat. Off. .
0398817 11/1990 European Pat. Off. .

OTHER PUBLICATIONS

Takigawa et al., Cell Biol Int Rep 9(7):619–626 (1985).
Lutty et al., J Cell Sci 76(0):53–66 (1985).
*Journal of Cellular Biochemistry*, Suppl. O,Nr. 14, Teil C, 1990, H. Drexle et al.: "Natural inhibitors of endothelia cell proliferation".
*Science*, vol. 248, No. 4961, Jun. 1990, M. A. Moses et al.: "Identification of an inhibitor of neovascularization from cartilage".
*Experimental Cell Research*, vol. 188, No. 2, Jun. 1990, D. Vilette et al.: "Identification of an endothelial cell growth-inhibitory activity produced by human monocytes".
*European Journal of Immunology*, vol. 20, 1990, P. Seckinger et al.: "Tumor necrosis factor inhibitor: purification, NH2-terminal amino acid sequence and evidence for anti-–inflammatory and immunomodulatory activities".
WO, A, 9111193, Aug. 8, 1991.
Chang et al., "Amino Acid Analysis At The Picomole Level," *Biochem. J.* 199:547–555 (1981).
Crum et al., "A New Class of Steriods Inhibits Angiogenesis in the Presence of Heparin or a Heparin Fragment," *Science* 230:1375–1378 (1985).
D'Amore and Braunhut, "Stimulatory and Inhibitory Factors in Vascular Growth Control," *Endothelial Cells*, 2:13–37 (1988).
D'Amore et al., "Endothelial Cell Mitogens Derived From Retina and Hypothalamus: Biochemical and Biological Similarities," *J. Cell Biol.* 99:1545–1549 (1984).

Folkman, "Toward an Understanding of Angiogenesis: Search and Discovery," *Perspectives in Biology and Medicine* 29:10–36 (1985).
Ingber and Folkman, "Inhibition of Angiogenesis Through Modulation of Collagen Metabolism," *Lab. Invest.* 59:44–51 (1988).
Knecht and Chang, "Liquid Chromatographic Determination of Amino Acids After Gas–Phase Hydrolysis and Derivatizaiton with (Dimethylamino)Azobenzenesulfonyl Chloride," *Anal. Chem.* 58:2375–2379 (1986).
Lee and Valee, "Expression of Human Placental Ribonuclease in *Escherichia coli*," *Biochemical and Biophysical Research Communications* 160:115–120 (1989).
Lee et al., "Primary Structure of Human Placental Ribonuclease Inhibitor," *Biochemistry* 27:8545–8553 (1988).
Lowry et al., "Protein Measurement with the Folin Phenol Reagent," *J. Biol. Chem.* 193:265–275 (1951).
Polverini and Novak, "Inhibition of Angiogenesis by the Antineoplastic Agents Mitoxantrone and Bisantrene," *Biochem. Biophys. Res. Comm.* 140:901–907 (1986).
Rastinejad et al., "Regulation of the Activity of a New Inhibitor of Angiogenesis by a Cancer Suppresor Gene," *Cell* 56:345–355 (1989).
Robin et al., "The Histopathology of Corneal Neovascularization," *Arch. Ophthamol.* 103:284–287 (1985).
Shapiro and Vallee, "Human Placental Ribonuclease Inhibitor Abolishes Both Angiogenic and Ribonucleolytic Activities of Angiogenin," *Proc. Natl. Acad. Sci. USA* 84:2238–2241 (1987).
Taylor and Folkman, "Protamine is an Inhibitor of Angiogenesis," *Nature* 297:307–312 (1982).
Wissler et al., "Structure and Function of a Monocytic Blood Vessel Morphogen (Angiotropin) for Angiogenesis in Vivo and Vitro: A Copper–Containing Metallo–Polyribonucleo–Polypeptide as a Novel and Unique Type of Monokine," *Protides Bio. Fluids.* 34 (1986), 525–536.

*Primary Examiner*—Michael G. Wityshyn
*Assistant Examiner*—Jean C. Witz
*Attorney, Agent, or Firm*—Lyon & Lyon

[57] ABSTRACT

In order to isolate an inhibitor of the proliferation of endothelial cells from the tissue of vertebrates the tissue selected as the starting material e.g. embryonic tissue or adult brain tissue from birds or mammals, is centrifuged, homogenized and subsequently the tissue extract is applied to a cation exchanger and the substances which bind to the cation exchanger are subjected to a fractionation, the active fractions are separated by gel filtration chromatography and they are purified by reverse phase HPLC. The new inhibitor obtained in this way is suitable for treating disease states in which an inhibition of capillary growth is necessary such as for the treatment of tumors, rheumatoid arthritis, diabetic retinopathy and retrolental fibroplasia and for treating wounds in order to regulate the regeneration of blood vessels.

14 Claims, 5 Drawing Sheets

INHIBITORS OF ENDOTHELIAL CELL PROLIFERATION

The formation of new capillary vessels (angiogenesis) proceeds in an ordered series of steps: at a point at which a new vascular bud begins to grow out (usually in the region of post-capillary venules) the endothelial cells locally degrade the basal membrane, migrate towards the source of the factor stimulating angiogenesis, grow and divide, form a vascular lumen and land on other vascular buds or existing capillaries so that a new capillary section forms which finally surrounds itself with a newly formed basal membrane.

The angiogenic activity is usually almost completely inhibited in adult individuals. More intense angiogenic processes only occur in wound healing and in females in connection with the ovarian cycle. However, in general the turnover rate of endothelial cells in the organism is low. The complete renewal of an existing endothelial cell population takes years, there are however substantial organ and tissue-specific differences (Folkman, Medicine 29 (1985), 10–36).

The usual strict control under which angiogenesis normally stands is abolished during the growth of solid tumours. A strong angiogenesis is absolutely necessary for the growth of tumours with a diameter of over 1 to 2 mm. Thus avascular tumours remain limited to a very small size due to the limited diffusion in the supply of gases and nutrients and in removing waste products. The deficiency in the capability of solid tumours to grow to a clinically significant size or to form metastases in the absence of a successful induction of angiogenesis has created great interest in research into compounds which inhibit angiogenesis.

The commercial application of such inhibitors is in the inhibition of tumour growth in general, in particular in the inhibition of tumours based on endothelial cells such as Kaposi's sarcoma and haemangiomas. In addition a therapeutic use for other diseases is also possible which are due to excessive capillary growth. Particular examples of this are diabetic retinopathy and retrolental fibroplasia, both of which are eye diseases. A further possible application is the treatment of wounds whereby an inhibitor of angiogenesis can be used to regulate wound healing i.e. in delaying the regeneration of blood vessels. In addition an angiogenesis inhibitor can also be used for the treatment of rheumatoid arthritis. In this disease a vascularization of cartilage is observed (as generally seen in every inflammation in this region) which can be suppressed by an angiogenesis inhibitor.

A series of extracts which inhibit angiogenesis have been prepared from avascular tissues (see D'Amore and Braunhut, in Endothelial Cells, Vol. II, published by U.S. Ryan, CRC Press, Boca Raton, Fla., 13–37). Anti-inflammatory agents also suppress angiogenesis (Robin et al., Arch. Ophthamol. 103 (1985), 284–287; Polverini and Novak, Biochem. Biophys. Res. Comm. 140 (1986), 901–907), such as e.g. protamine (Taylor and Folkman, Nature 297 (1982), 307–312), angiostatic steroids (Crum et al., Science 230 (1985), 1375–1378), a placental RNAse inhibitor (Shapiro and Vallee, Proc. Natl. Acad. Sci. USA 84 (1987), 2238–2241) and a series of compounds which influence matrix synthesis and stability (see e.g. Ingber and Folkman, Lab. Invest. 59 (1988), 44–51). An inhibition of tumour growth or regression was found in vivo for some of these inhibitors but not in all tumours. Moreover the toxicity of these angiogenesis inhibitors also remains a problem.

An angiogenesis inhibitor was found by Rastinejad et al. (Cell 56 (1989), 345–355) in a medium with hamster cells and hamster-human hybrid cells which suppresses neovascularization in vivo. This compound is apparently a glycoprotein with a molecular weight of 140 kDa. However, this inhibitor has only a low stability and in particular it is not thermally stable.

DE 40 06 609 discloses a protein which acts as an inhibitor of the proliferation of endothelial cells obtainable from baby hamster kidney cells which has a molecular weight of ca. 60 to 100 kDa in gel filtration under native conditions and has a higher thermal stability.

The object of the present invention was to provide further angiogenesis inhibitors which can be used therapeutically as an alternative and supplement to already known inhibitors.

The object according to the present invention is achieved by a process for the isolation of inhibitors of the proliferation of endothelial cells from the tissue of vertebrates which is characterized in that (a) the tissue selected as starting material is homogenized and subsequently centrifuged, (b) the tissue extract is applied to a cation exchanger and the substances which bind to the cation exchanger are subjected to a fractionation, (c) the active fractions from step (b) are separated by gel filtration chromatography and (d) the active fractions from step (c) are purified by reverse phase HPLC.

The tissue from vertebrates selected as the starting material for the process according to the present invention can be of embryonic as well as of adult origin. Embryonic tissue from birds or mammals is preferably used, tissue from chicken embryos is particularly preferred as the starting material. In addition it is preferred that adult brain tissue from birds or mammals, in particular adult bovine brain, be used as the starting material. However, it should be pointed out that the process according to the present invention can also be applied to human tissue (of embryonic as well as of adult origin).

If chicken embryos are used as the starting material for the process according to the present invention then two substances can be isolated by this means which are active as inhibitors of the proliferation of endothelial cells. These two substances are denoted EMBIN I and ANEMIN. If adult bovine brain is used as the starting material then, when the isolation procedure is carried out in an analogous manner, two substances with inhibitory activity are likewise obtained whose biochemical properties and molecular weight according to SDS gel electrophoresis correspond to the two inhibitors from chicken embryos. It has not yet been possible to clarify whether the substances from the various starting materials are identical to one another or whether they are only very closely chemically related to one another. It should, however, be made clear that these substances and their respective species-specific analogues can also be obtained from other vertebrates in particular birds and mammals.

The inhibitor of endothelial cell proliferation designated EMBIN I which can be obtained by the process according to the present invention is characterized in that it yields one band with an apparent molecular weight in the range of 2.5 to 6.2 kDa on gel electrophoresis in SDS polyacrylamide gel.

EMBIN I also shows an undiminished inhibition of endothelial cell proliferation even after a 60 minute incubation at 90° C. Thus EMBIN I proves to be a very heat resistant compound when one bears in mind that only very few proteins can withstand such a treatment while retaining their activity.

In addition it was established that EMBIN I is resistant to a number of different proteases. The following proteases were tested in this connection: trypsin, S. aureus V8 protease, clostripain, thermolysin, subtilisin, pronase E, proteinase K, carboxypeptidase Y, papain, pepsin (Sigma), chymotrypsin, pyroglutamate aminopeptidase, endoproteinase Arg-C, endoproteinase Lys-C (Boehringer Mannheim), proline specific endopeptidase (Seikagaku Kogyo, Japan). In these experiments each of the tested proteases were dissolved in their requisite buffers and incubated with an aliquot of EMBIN I under the conditions given by the manufacturer for the respective enzyme. In none of the experiments was there a change in the inhibitory activity or the migration characteristic of EMBIN I in the gel.

In order to examine whether EMBIN I may be present as a peptide associated with nucleic acid molecules, which is for example true for the angiogenesis factor "angiotropin" (Wissler et al., Protides Bio. Fluids. 34 (1986), 525–536), EMBIN I was incubated with DNAse as well as with RNAse. No change in the migration characteristics was found during gel electrophoresis.

On the basis of the consideration that EMBIN I could be a glycopeptide, digestions were carried out with glycolytic enzymes. For this EMBIN I was subjected to a sequential digestion, firstly with neuraminidase and afterwards with β-galactosidase. EMBIN I was in addition treated with glycopeptidase F. Furthermore it was examined whether EMBIN I shows a reaction with the "Glycan detection kit" from the Boehringer Mannheim Company. However, the presence of a glycosylation could not be detected in any of these experiments.

Lipid extractions of EMBIN I and ANEMIN have up to now given no indication that lipid components are present.

An incubation with diethylpyrocarbonate was carried out to investigate the question whether EMBIN I is a substance of protein character. Diethylpyrocarbonate reacts with free α amino groups or with the ε amino groups of lysine to form an N-carboxy derivative. When EMBIN I is treated with diethylpyrocarbonate it was found that the inhibitory activity is completely abolished. This indicates that the inhibitory activity of EMBIN I is based on one or several functionally important amino groups. The fact that the inhibitory activity of EMBIN I can also be abolished by treatment with phenol is a further indication for the peptide character of this substance. It was also established that EMBIN I can be stained with the ninhydrin spray reagent (which serves as a test for amino groups).

A further indication that EMBIN I is a peptide is that a protein determination according to the Lowry method (Lowry et al., J. Biol. Chem. 193 (1951), 265–275) is possible.

The amino acids ASX (Asn or/and Asp), GLX (Gln or/and Glu), Pro, Val, Leu, Lys and His were detectable by amino acid analysis of EMBIN I (hydrolysis with 6N HCl and subsequent derivatization with 4-dimethylamino-azobenzene-4'-sulfonyl chloride according to Knecht and Chang, Anal. Chem. 58 (1986), 2375–2379). Characteristic peaks for Ser, Thr, Arg, Gly, Ala, Ile, Phe and Tyr were also found, however, the amounts detected were too low to definitely confirm their presence.

Present results on the characterization of EMBIN I indicate that it is a small basic peptide but other possibilities cannot yet be excluded. If one assumes that EMBIN I is a peptide then the N-terminus of the molecule seems to be blocked since it has not as yet been possible to sequence EMBIN I according to the method of Edman which requires a free α amino group of the peptide.

A further unusual property of EMBIN I is the difference in its migration characteristics during gel filtration on the one hand and SDS PAGE on the other hand. On a gel filtration column the EMBIN I activity is eluted at a position which corresponds to a molecular weight of about 500 to 1000 Da. However, when the active fractions are examined by SDS PAGE the EMBIN I bands are found in the region between about 2.5 and 6.5 kDa independent of the electrophoresis system used.

The other inhibitor ANEMIN obtainable by the process according to the present invention also shows this difference in migration properties during gel filtration and SDS PAGE. For ANEMIN a band is found in SDS PAGE in the 16 to 20 kDa range whereas according to gel filtration the molecular weight should be less than 1000 Da. ANEMIN like EMBIN I also has a very high stability and resistance to proteases.

Although neither the structure of EMBIN I nor that of ANEMIN has been elucidated in detail it was possible to produce them in a repeatable manner according to the present invention as pure substances since both inhibitors can be detected in the SDS gel as single bands without significant impurities.

In the following it is intended to elucidate the individual steps of the process according to the present invention in more detail. Step (a) is the homogenization and centrifugation of the tissue selected as the starting material. Adult bovine brain or 4 to 10 day old chicken embryos are preferably used as the starting material. However, other types of tissue, in particular embryonic tissue or brain tissue from other species, are also suitable. A tissue extract is obtained by homogenizing the tissue and subsequent centrifugation which can be introduced into the following steps in the procedure. The homogenization and centrifugation steps can be carried out according to the usual methods known to a person skilled in the art and are not particularly critical for the process according to the present invention.

Step (b) of the process according to the present invention consists in applying the tissue extract to a cation exchanger and subjecting substances which bind to the cation exchanger to a fractionation. The inhibitors according to the present invention are able to bind to a cation exchanger under approximately neutral pH conditions and salt concentrations of up to 100 mmol/l whereas a majority of the substances present in the tissue extract are not able to do this. Elution of the substances according to the present invention from the exchanger column can for example be carried out by increasing the salt concentration to 700 mmol/l. A CM Sepharose matrix (Pharmacia/LKB) has for example proven to be a suitable cation exchanger. However, other cation exchangers can also be used.

Fractions from the cation exchanger eluate which show an inhibition of the proliferation of endothelial cells in an in vitro activity test (infra) can be separated by gel chromatography according to step (c) of the process according to the present invention. However, it is preferred that, after fractionation over the cation exchanger, the active fractions are firstly additionally applied to a hydroxylapatite column and then the eluate of the hydroxylapatite column is subjected to ultrafiltration. In the hydroxylapatite chromatography only a very small amount of protein is not bound to the hydroxylapatite matrix. Since the inhibitors according to the present invention are located in the eluate of the column (i.e. they do not bind), a good purification effect is achieved by this step.

Before the gel filtration step an ultrafiltration was carried out in order to reduce the volume of the active protein fraction present after the hydroxylapatite chromatography. Due to the low molecular weight of the inhibitors the concentration is carried out over a 500 Da membrane. After this the substances with inhibitory activity are located in the retentate, the filtrate does not have any sort of inhibitory effect on the proliferation of endothelial cells.

The ultrafiltration can additionally be utilized to extensively desalt the sample by means of two diafiltration steps. Afterwards the volume of the sample is about 1/6 to 1/10 of the initial volume. A further concentration can be achieved by subsequently lyophilizing the sample and taking up the lyophilisate in a minimal volume of 0.2M acetic acid. The gel filtration column on which the sample is subsequently applied can also be equilibrated with this buffer.

Step (c) of the process according to the present invention is a gel chromatographic separation of the previously obtained active fractions. Biogel P2 which has a nominal exclusion size of about 1.8 kDa has proven to be a suitable material for the gel filtration. The substances with inhibitory activity are not eluted in the void volume of the column under the selected conditions. Consequently the inhibitory substances should have a molecular weight of less than 1800 Da, on the other hand it is possible that strong specific interactions with the matrix lead to an unusually strong retardation of the substances and thus simulate a molecular weight which is too low. After separating aliquots of the active fractions from the gel filtration by SDS PAGE and subsequent staining with silver, several bands could be visualized whose molecular weights are between 2.5 and 20 kDa. On the basis of this pattern of bands those fractions are pooled for the further course of isolation which have a broad band between 2 and 6 kDa which are referred to in the following by the term EMBIN I. The fractions which showed a broad band in the region between 14 and 20 kDa were also pooled. The inhibitory effect associated with these fractions was designated ANEMIN and was purified separately from EMBIN I in the following.

Step (d) of the process according to the present invention for the isolation of substances with inhibitory activity is a purification by reverse phase HPLC. Column matrices from various manufacturers coated in different ways were used for the reverse phase HPLC and the elution agent was a trifluoroacetic acid/acetonitrile gradient. However, in this procedure the substances with inhibitory activity could not be bound to the column but were instead regularly located in the portion of unbound substances. It was apparent from a gel-electrophoretic analysis of the individual fractions that a broad band with a molecular weight in the range 2.5 to 6.5 kDa (EMBIN I) was present in the fraction with inhibitory activity.

Due to the good pH stability of the polyvinyl matrix of the Asahipak ODP50 column it was possible to carry out a chromatography in an alkaline environment without having to add alkylammonium ions that are necessary when using other silica materials. When the reverse phase HPLC is carried out at a pH value of 12.5 it was found that EMBIN I binds to the column matrix. When the fractions with inhibitory activity were analysed on a polyacrylamide gel it was found that a broad band is present in the molecular weight range of 2.5 to 6.2 kDa.

In addition is has also proven to be advantageous to carry out the HPLC wash in the presence of an acidic ion pair former. Organic sulfonic acids, in particular alkyl or aryl sulfonic acids, are suitable as acidic ion pair formers. These sulfonic acid molecules can on the one hand interact with the hydrophobic groups of the column matrix via their hydrophobic alkyl component while at the same time they can bind positively charged substances via their sulfonic acid groups. The concentration of the sulfonic acid is preferably between 0.1 and 50 mmol/l, particularly preferably between 1 and 10 mmol/l.

It was in fact established that EMBIN I binds to an Asahipak ODP 50 column equilibrated with 5 mmol/l heptanesulfonic acid, pH 3.5 and can be eluted again in a linear gradient.

The fractions of the gel chromatography containing ANEMIN can also be further purified by reverse phase HPLC similarly to EMBIN I e.g. in the presence of heptanesulfonic acid as the ion pair former. In polyacrylamide gel electrophoresis the ANEMIN bands are found in the range between 16 and 20 kDa.

The inhibitors of endothelial cell proliferation designated EMBIN I and ANEMIN can be produced as pure substances by the process according to the present invention in which tissue from chicken embryos is used as the starting material. If adult bovine brain is used as the starting material then it is possible by using identical steps in the procedure to obtain two corresponding substances which have the mobility properties of EMBIN I and ANEMIN in polyacrylamide gel electrophoresis.

The activity of the substances with inhibitory activity was analysed in vitro by the BAEC test and in vivo by the CAM test which are described in detail in the following example 1.

The substances according to the present invention can be used in the treatment of all diseases in which an increased angiogenesis takes place and which were already mentioned above. In particular the substances according to the present invention can be used to inhibit growth of tumours, such as Kaposi's sarcomas or haemangiomas, for the treatment of eye diseases in which increased capillary growth occurs in particular diabetic retinopathy and retrolental fibroplasia, as well as in rheumatoid arthritis or to regulate wound healing.

The dose per kg body weight of the substances according to the present invention which are preferably used should be of the order of µg up to a maximum of mg.

Figure 2:
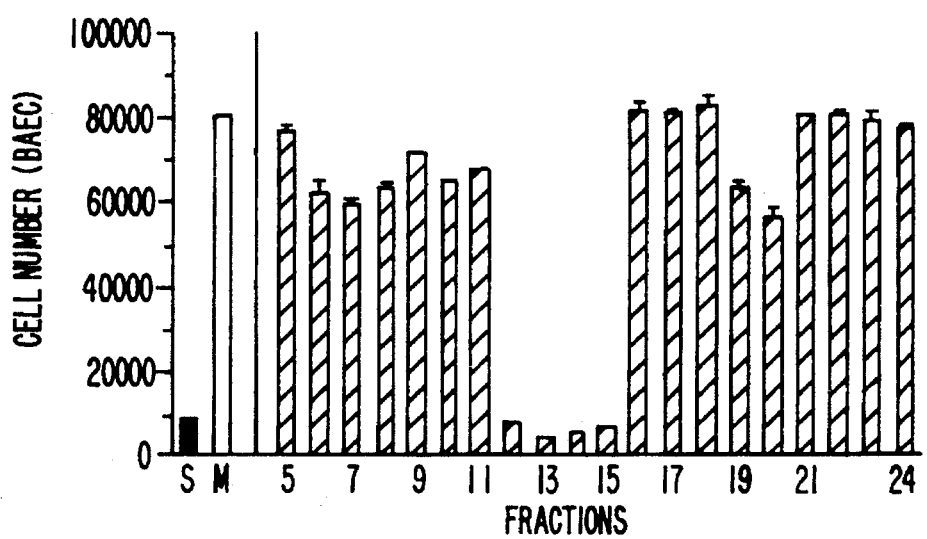
Figure 3:
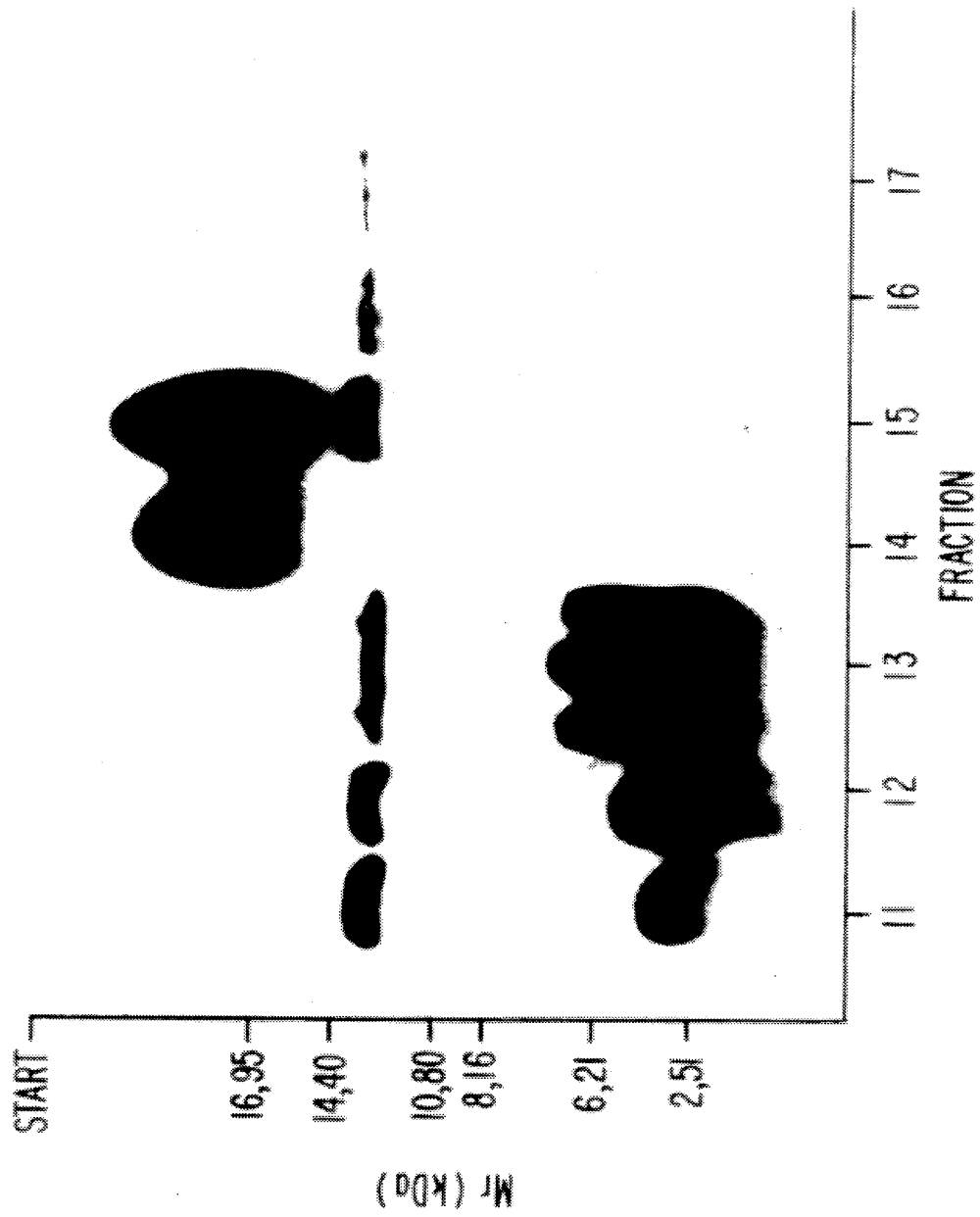
Figure 4:
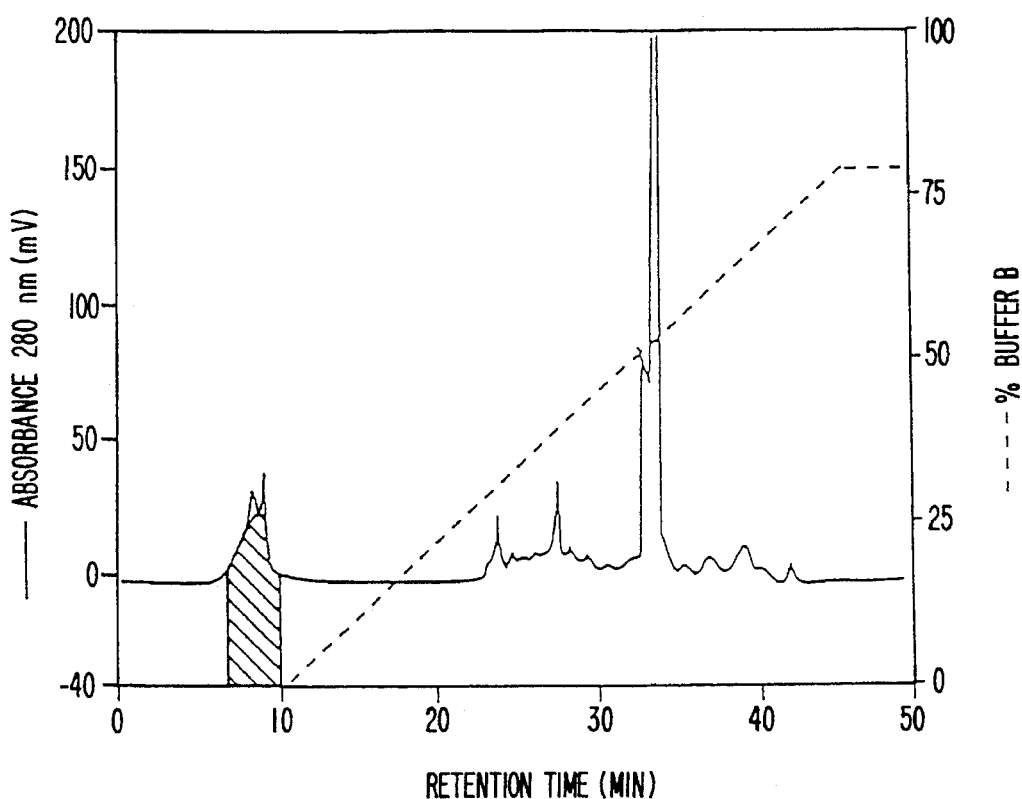
Figure 5:
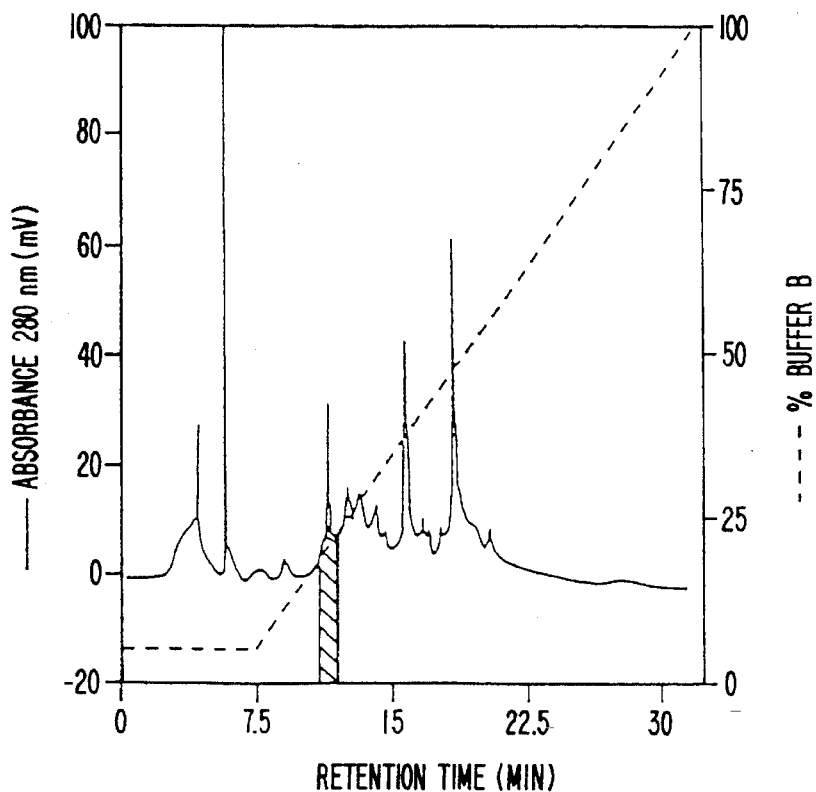
Figure 6:
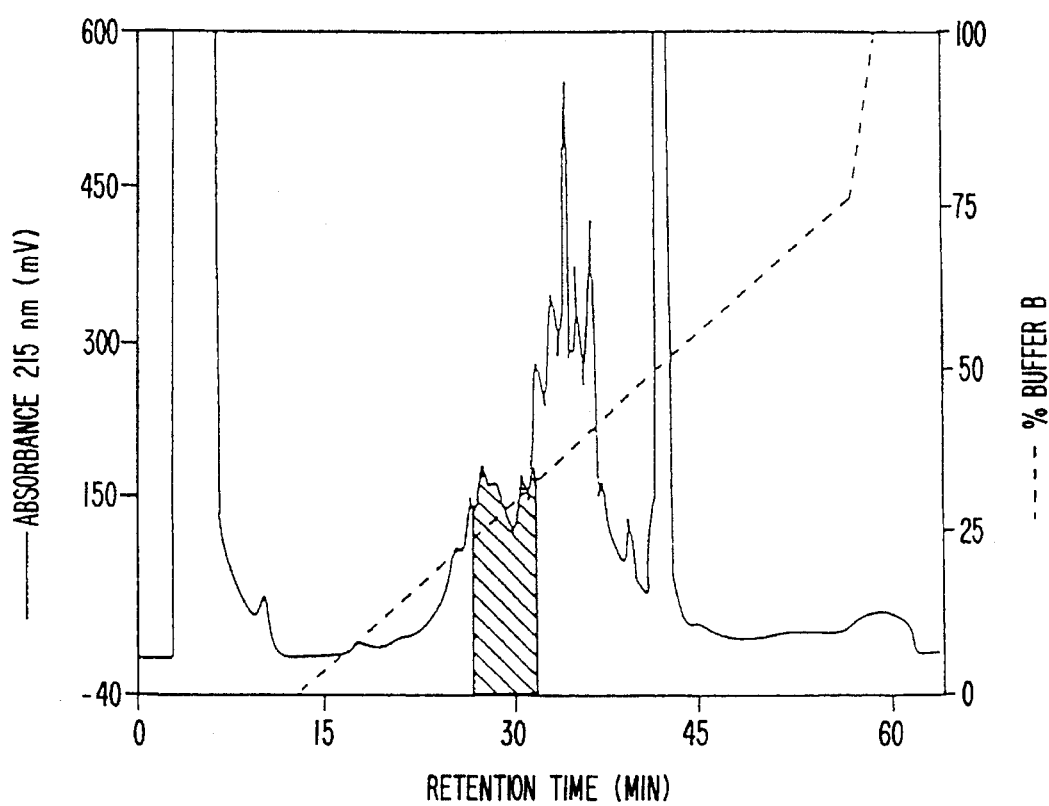
Figure 7:
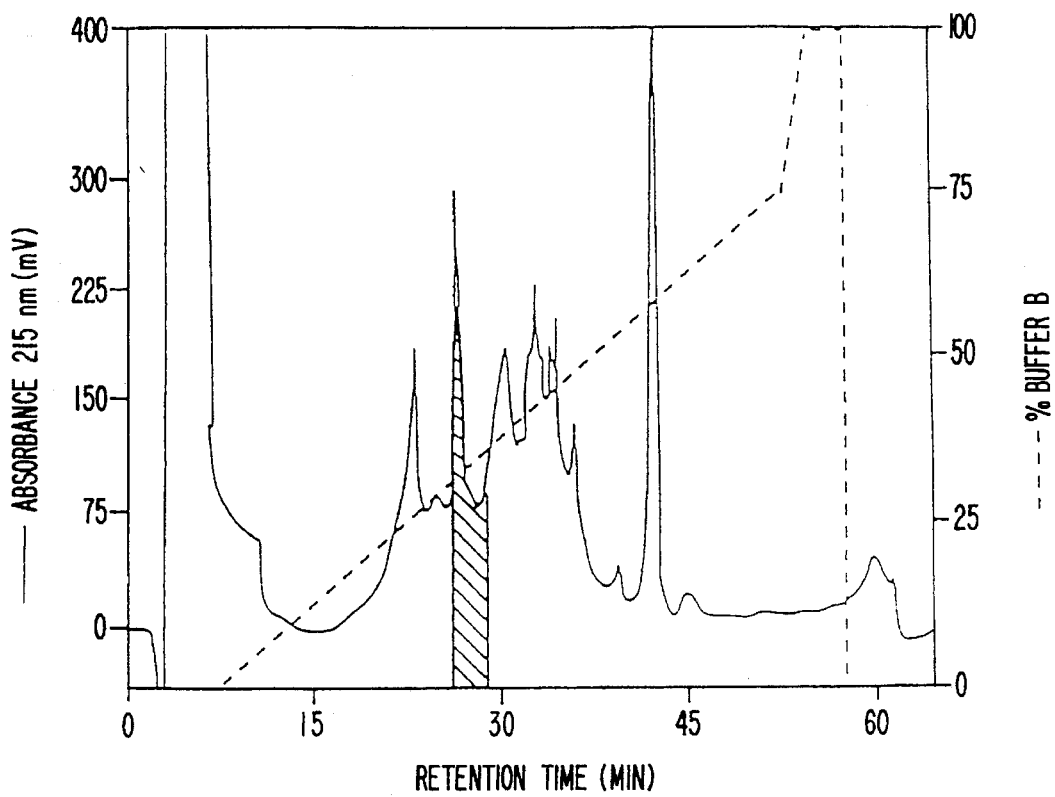
Figure 8:
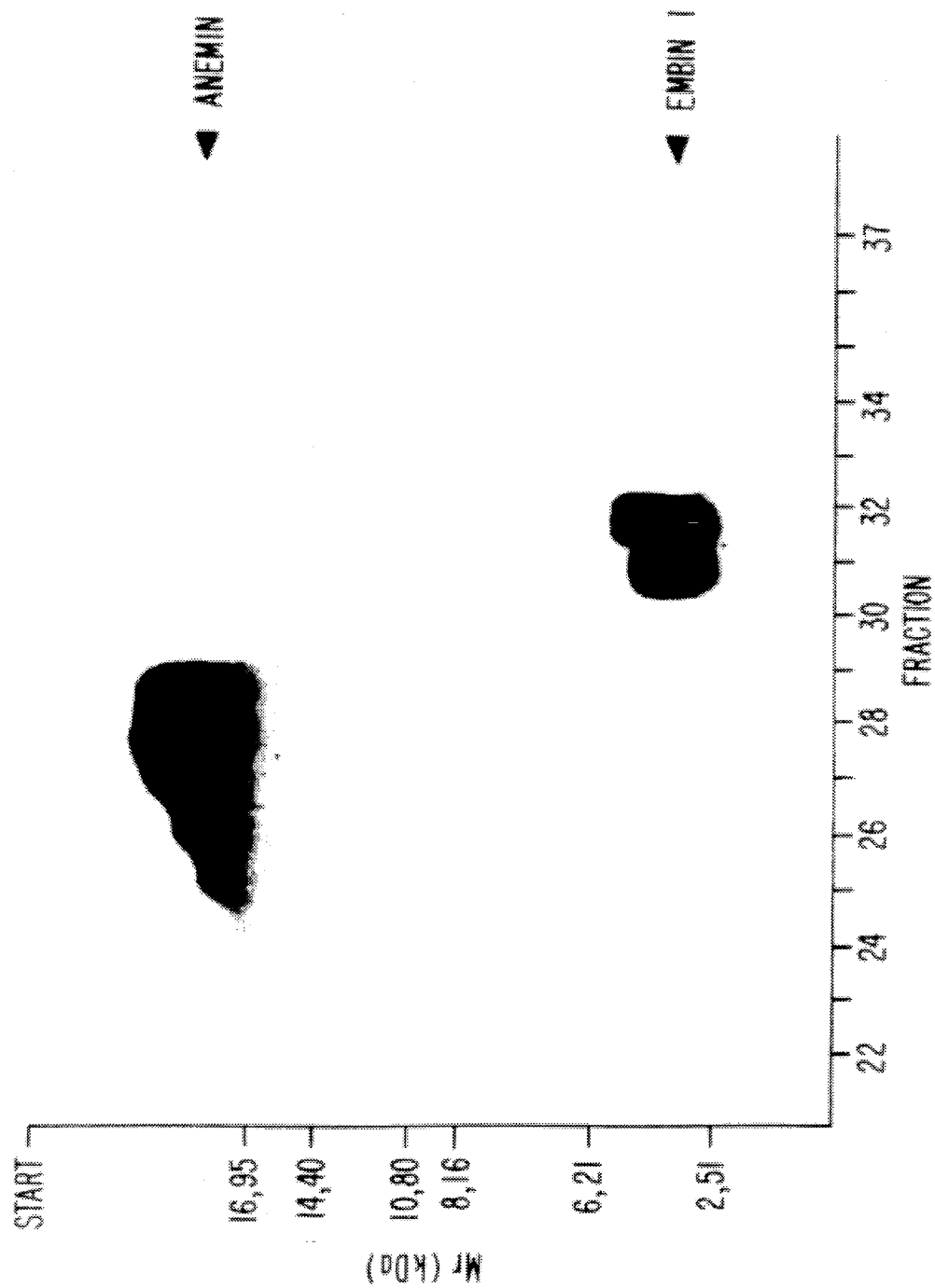

The following examples are intended to elucidate the invention in conjunction with the figures. The figures show:

FIG. 1: a gel filtration chromatography of the tissue extract from chicken embryos, FIG. 2: the inhibiton of endothelial cell proliferation by fractions from the gel chromatography, FIG. 3: the protein pattern of fractions 11–17 from the gel filtration, FIG. 4: the elution profile of EMBIN I in RP-HPLC in TFA/acetonitrile, FIG. 5: the elution profile of EMBIN I in RP-HPLC at pH 12.5, FIG. 6: the elution profile of EMBIN I in the presence of hetanesulfonic acid, FIG. 7: the elution profile of ANEMIN in RP-HPLC in the presence of heptanesulfonic acid, FIG. 8: a SDS-PAGE of ANEMIN.

EXAMPLE 1

Detection of inhibitory activity in the proliferation test
Preparation of retinal factor Retinal factor is an aqeuous extract from bovine retinae which mainly contains bFGF (basic fibroblast growth factor; Mascarelle et al. 1987) as the endothelial cell mitogen.

The retinae from 25–50 bovine eyes were freed by dissection and incubated until the next day at 4° C. with the same volume of PBS (phosphate-buffered saline solution)

(D'Amore et al., J. Cell Biol. 99 (1984), 1545–1549). The preparation was carefully stirred several times. Firstly the solid components were removed by a ten minute centrifugation at 1000 rpm (Heraeus), the supernatant was subsequently centrifuged again for 30 min at 45000 g (Sorvall, SS34). The supernatant of the second centrifugation was aliquoted and frozen at −20° C. The aliquots were sterile filtered before use (0.2 or 0.45 μm pore size).

BAEC test

Endothelial cell cultures which were obtained from bovine aortae (BAEC; bovine aortic endothelial cells; passage 6–17) were used to test the inhibition of endothelial cell proliferation. For the activity test 10–15000 BAEC were sown per well at the beginning (day 1) in a cell culture plate with 24 wells (Costar) in Dulbecco's modified minimal medium (DMEM) containing 5% foetal calf serum (FCS) that attached themselves to the plastic surface within the next 6–8 hours.

On the following day (day 2) non-adherent cells were removed together with the old culture medium and exchanged for DMEM containing 5% FCS and 40 μl/ml retinal factor. The proliferation of endothelial cells is strongly stimulated by the addition of retinal factor to the medium. After changing the medium the samples to be tested were added (up to 40 μl/well). The cells were incubated for another 3 days at 7.5% $CO_2$ and at 37° C., afterwards (day 5) the number of cells was determined in a Coulter counter. This experimental concept was used to examine the samples to be investigated for the content of substances that can inhibit the proliferation of endothelial cells even in the presence of mitogens.

Determination of cell numbers

After the 72 hour incubation period the cells were washed with calcium-free and magnesium-free PBS, detached from the support by trypsination (0.5 ml 0.05% trypsin/0.02% EDTA solution, Gibco) and transferred into 9.5 ml isotonic solution. The determination of cell numbers was carried out in a Coulter counter, Industrial D (Attenuation: 2; Aperture Current; 0.0093; Threshold: 12; capillary diameter: 200 μm). The graphical analysis of the data obtained was carried out using the programs "Cricket Graph" and "Kaleidagraph" on computers of the Apple Co.

SMC and 3T3 tests

The proliferation tests with smooth muscle cells (SMC) and NIH 3T3 fibroblasts were carried out according to the same method. In contrast to BAEC the stimulation of the proliferation of SMC and 3T3 fibroblasts in the presence of 10% FCS in the culture medium is adequate and it is not necessary to add retinal factor.

In vivo test (CAM test) for inhibition

Eggs for hatching from the Hölzl Co. (Wasserburg am Inn) were each incubated at 37° C. and 70–80% air humidity in an egg incubator and each of the eggs was turned automatically after 6 hours. On day E3 windows with a diameter of ca. 1 cm were cut into the shells of fertilized three day old chicken eggs so that later the factors embedded in methylcellulose could be applied on the CAM. For this a piece of Scotch adhesive tape was first stuck onto the upper side of the egg shell. Then 2–3 ml egg white was withdrawn from the pointed side of the egg using a 10 ml syringe and a strong cannula in order to slightly lower the embryo which swims on top of the egg yolk. A hole was then cut in the egg shell in the middle of the adhesive strip using pointed scissors. In this way the possibility of egg shell fragments falling onto the CAM can be largely avoided. These shell fragments can themselves cause a reaction similar to angiogenesis. The hole in the egg shell was subsequently closed with a second strip of Scotch adhesive tape and the eggs were incubated for a further 3–4 days under the same conditions.

The fractions to be tested were mixed with the same volume of a sterile 1% methylcellulose solution (4000 cpi; Sigma) in a ratio of 1:1. 10 μl of each was pipetted onto the polished cut surface of Teflon rods (d=3 mm) and dried under a sterile hood. Using a fine pair of forceps it was possible to peel off the small methylcellulose discs from the Teflon rods and carefully place them on the CAM on day E6 or E7 of development.

After 48 or 72 hours the regions of the CAM in the vicinity of the methylcellulose discs were examined under a binocular for angiogenesis inhibition. In order to contrast the vascular net, 20 μl of a solution of 40% Luconyl blue (Hoechst) in PBS was injected into an allantois vein of the embryos using a glass capillary.

Ca. 240 ng EMBIN I was used per methylcellulose disc (n=39). An avascular zone was observed at the edge of 4 discs, a regeneration of blood vessels which was only slight was detectable among 6 discs. In the remaining embryos no change in the vascular pattern could be observed.

EXAMPLE 2

Methods for isolating EMBIN I and ANEMIN

Starting material

Eggs for hatching from the Hölzl Co. (Wasserburg am Inn) were used as the starting material. 4–10 days after starting the incubation of the eggs they were opened over a large petri dish and the embryos were removed. The anmiotic skin and above all the allantois were dissected from the embryos as completely as possible in order to exclude influences from the allantoic liquid which represents the embryonic urine. The embryos were stored frozen at −20° C. until the extraction and were thawed overnight at 4° C. before beginning the preparation.

Preparation of the extracts

2500–3500 chicken embryos on days E4 to E10 of development, corresponding to a wet weight of 1.8 to 3 kg were homogenized in portions of 300 g with a total of 1.5 to 2 l extraction buffer (20 mM MOPS pH 6.8/100 mM NaCl/2 mM PMSF) in a kitchen mixer from the Braun Co. The homogenate was subsequently extracted for 30 min at 4° C. while stirring and the insoluble components were separated by a 90 minute centrifugation at 22000 g (Sorvall, GSA rotor).

Cation exchange chromatography on CM Sepharose fast flow

The extract obtained in the first step was pumped onto a CM Sepharose column (Pharmacia/LKB, Freiburg; 50×250 mm) which had been equilibrated with application buffer (20 mM MOPS pH 6.8/100 NaCl). The flow rate was 500 ml/h. After the extract had been applied, the column was washed with application buffer until the absorbance had reached a minimum at 280 nm. 86% of the total protein was located in the eluate. The proteins bound to the column, which also included the substances with inhibitory activity EMBIN I and ANEMIN, were subsequently eluted in a step with 700 mM NaCl in 20 mM MOPS pH 6.8.

Chromatography on hydroxylapatite

The gel bed for this was packed at a flow rate of 50 ml/h after the dry hydroxylapatite powder (Bio-Gel HTP, BioRad Co., Munich) had been sufficiently swollen in the application buffer (20 mM MOPS, pH 6.8). The eluate from the cation exchange chromatography was then applied directly in 2–3 portions at 40 ml/h onto the hydroxylapatite column (25×100 mm) equilibrated in 20 mM MOPS pH 6.8 which was subsequently washed with the equilibration buffer until the absorbance at 280 nm was at a minimum. Only a very small portion of protein (including the substances with inhibitory activity) was not bound by the hydroxylapatite matrix and was located in the column eluate.

The material which was reversibly bound to the hydroxylapatite matrix could be eluted by 0.4M potassium phosphate buffer pH 6.8. This eluate was subsequently dialysed against 2×5 l 20 mM MOPS buffer pH 6.8 or against 0.5× PBS pH 7.2. Visking dialysis tubes were usually used for this which have a nominal separation limit of 10–15 kDa.

Desalting and concentration by ultrafiltration

The material which was not bound to hydroxylapatite was concentrated over a YC05 ultrafiltration membrane (Amicon GmbH, Witten, nominal exclusion limit: 500 Da) in an ultrafiltration cell (Amicon GmbH, Witten; type 8400) to about a 10th of the initial volume. The solution was desalted in the same chamber by diafiltration with distilled water.

Gel filtration

The largely desalted concentrate from the ultrafiltration was lyophilized in order to further reduce the solvent volume. A Bio-Gel P2 column (Bio-Rad Co., Munich; 200–400 mesh; nominal exclusion limit: 1800 Da) which had been equilibrated in 0.2M acetic acid was used for the gel filtration of the lyophilisates which had each been taken up in. ca. 4–6 ml 0.2M acetic acid. The sample was applied to the column by means of a peristaltic pump (LKB/Pharmacia) and the gel filtration was carried out by pumping the eluting agent onto the column. The flow rate during the gel filtration was 6 ml/h, the separated proteins and peptides were detected at 280 nm. The column eluate was collected in fractions (UltroRac; LKB; 40 min/fraction).

FIG. 1 shows the gel filtration chromatography on a Biogel P2 column. The largest portion of the proteins and peptides applied to the column are eluted in the exclusion volume (fractions 5–10). Fractions 17–20 contain the salt which is still present and at the same time mark the lower exclusion limit of the column. The fractions from the gel filtration were lyophilized in order to remove the acetic acid and each was taken up in 4 ml redistilled H$_2$O. FIG. 2 shows the inhibition of endothelial cell proliferation in the fractions after gel filtration. (S) and (M) show the cell numbers at the time of sample application and after maximum proliferation. The effect triggered by aliquots from fractions 5–24 on endothelial cell proliferation is represented by the corresponding column height.

FIG. 3 shows a separation of aliquots from fractions 11–17 by SDS PAGE and subsequent silver staining. Several bands are visible whose molecular weights are between 2.5 and 20 kDa. Based on the band pattern fractions 11–13, which show a prominent band at 13 kDa and several weaker bands in addition to a broad band between 2 and 6 kDa (EMBIN I), are pooled for the remaining isolation process. Fractions 14 and 15 which show a broad band in the range between 14 and 20 kDa (ANEMIN) in addition to a band at 13 kDa were processed in the same way.

Reverse phase chromatography

All reverse phase chromatography steps were carried out on a HPLC apparatus from the Kontron Co. (Eching) with 2 HPLC pumps of the 420 type, a detector 430 and the data system 450. The data system 450 consists of a AT computer with implemented controlling software as well as software for recording and processing the recorded data. The separated substances were usually detected simultaneously at two wavelengths (in the region of the absorbance of the peptide bond at a wavelength between 214 and 220 nm, as well as at 280 nm, the absorbance of maximum tyrosine).

Reverse phase (RP) chromatography in a TFA/acetonitrile solvent system

Ready packed RP columns of several manufacturers were examined with regard to their suitability for the further purification of EMBIN I using a TFA/acetonitrile solvent system. The columns were equilibrated in buffer A (0.1% TFA; Rathburn, Scotland) and eluted by linear gradients with an increasing concentration of solvent B (0.09% TFA in 95% acetonitrile; Rathburn, Scotland). The experiments are summarized in Table I.

TABLE I

Summary of chromatography in the reverse phase mode for the isolation of EMBIN I. The flow rate was 1 ml/min, the fraction size was 1 min. The absorbance was recorded at 214 and 280 nm.

| Column type/size (in mm) | Coating | Gradient % A - % B; min |
|---|---|---|
| Vydac 214 TP/4.6 × 250 | C4 | 0–90; 50 |
| Aquapore 300/4.6 × 100 | C8 | 0–100; 15 |
| Asahipak ODP50/6 × 150 | C18 | 0–75; 35 |
| Spherisorb ODS2/ 4.6 × 250 | C18 | 0–95; 55 |

FIG. 4 shows the elution profile of a RP-HPLC using the Asahipak ODP50 column (C18 coating) as an example. From the gel electrophoretic analysis of the individual fractions it was apparent that the inhibitory activity is located in fraction 3 (shown by the hatching). A gel electrophoretic analysis shows a band with a molecular weight of 2.5 to 6.5 kDa which is EMBIN I.

Reverse phase chromatography under alkaline conditions

Buffer A: 10 mM Tris, adjusted to pH 12.5 with 5N NaOH
Buffer B: 10 mM Tris pH 10/80% acetonitrile After the Asahipak ODP50 column had been equilibrated in 5% buffer B, 500 µl of the YC05 concentrate of EMBIN I was admixed with the same volume of equilibration buffer and applied to the column (1 ml/min; 1 min/fraction; detection at 220 and 280 nm). The elution of substances bound under these conditions was carried out within 25 min using a linear gradient of 0 to 100% buffer B. The fractions were freed of solvent in a vacuum concentrator and each was taken up in 250 µl redistilled. H$_2$O.

FIG. 5 shows the elution of a sample containing EMBIN I at pH 12.5. The active fraction (determined by the BAEC test) is shown by the hatching. On electrophoresis in polyacrylamide gel the inhibiting fraction showed the EMBIN I band in the molecular weight range of 2.5 to 6.2 kDa.

Reverse phase chromatography using an ion pair former

The last purification step for EMBIN I was carried out on a 6×150 mm Asahipak ODP C18 column (Asahi Chemical Industry, Japan). Fractions from the gel filtration containing EMBIN I were dried in a vacuum concentrator and taken up in 5 mM heptanesulfonic acid pH 2.5 (Regis Chemical Company, Morton Grove, Ill., or Fluka Chemikalien, Ulm). 1 ml aliquots were applied to the column (equilibrated in 5 mM heptanesulfonic acid pH 2.5), the elution was carried out with a linear gradient of 0 to 100% 5 mM heptanesulfonic acid pH 2.5 in 90% acetonitrile for 35 min. The fractionated eluate was freed of solvent in a vacuum concentrator and the residues were taken up in redistilled water for further analysis.

FIG. 6 shows the elution profile of a sample containing EMBIN I in RP-HPLC in the presence of heptanesulfonic acid as the ion pair former. The fractions which were positive in the activity test (shown as a hatched area) displayed the EMBIN I band when separated by gel electrophoresis.

FIG. 7 shows the elution profile of ANEMIN in RP-HPLC with heptanesulfonic acid. The fractions which were positive in the BAEC activity test are shown as a hatched area. For this the lyophilized fractions 14 and 15 from the gel filtration were taken up in 2 ml of equilibration buffer and separated under the same conditions as above. In these fractions EMBIN I was also present in addition to ANEMIN.

FIG. 8 shows a SDS polyacrylamide gel of fractions 22–37 from the RP-HPLC of ANEMIN. Aliquots from each fraction were separated on a gel and the peptide bands were visualized by silver staining. According to this the ANEMIN band in the range between 16 and 20 kDa was present in fractions 25 to 29 whereas EMBIN I was still visible in fractions 31 and 32.

EXAMPLE 3

Biochemical characterization of EMBIN I

Thermostability

In each case 100 µl of a cation exchanger eluate having inhibitory activity on the proliferation of endothelial cells was heated to 90° C. in a water bath for 2, 5, 10 and 60 min. Afterwards the samples were placed on ice and after sterilization they were examined in the proliferation test for their inhibitory properties which still remained.

Protease resistance

The diafiltrated YC05 retentate before or after gel filtration chromatrography on BioGel P2 was used as a substrate to examine the ability to inactivate EMBIN I by treatment with various proteases. It was attempted to inactivate the inhibitory activity of EMBIN I using the following proteases: trypsin, S. aureus V8 protease, clostripain, thermolysin, subtilisin, pronase E, proteinase K, carboxypeptidase Y, papain, pepsin (Sigma); chymotrypsin, pyroglutamate aminopeptidase, endoproteinase Arg-C, endoproteinase Lys-C (Boehringer); proline-specific endopeptidase (Seikagaku Kogyo, Japan).

The proteases were dissolved in each case in their requisite buffers and incubated in an aliquot of EMBIN I substrate under the conditions stated for the respective enzyme. As a control of protease activity, BSA or lysozyme was incubated with the proteases in parallel experiments and the degradation of the proteins was checked by SDS PAGE. At the end of the incubation period the proteases were inactivated by heating the mixture for 5 min to 95° C., this was sterilized by filtration and examined in the BAEC test for inactivation of EMBIN I.

A corresponding aliquot of EMBIN I without enzyme but with the volumes of digestion buffer used in the various mixtures was incubated as a positive control under the same conditions and tested in the BAEC test.

Resistance to RNase and DNase

In each case 20 µl of the diafiltered YC05 retentate was firstly admixed with 1 µl of a 1M Tris/HCl solution pH 7.5 and in the case of the DNase mixture additionally with 1 µl of a 0.1M magnesium chloride solution. After adding in each case 1 µl of enzyme (Boehringer Mannheim), it was incubated for 30 min at 37° C., the digestion was subsequently stopped by addition of 10 µl sample buffer and the mixtures were examined by gel electrophoresis.

Sequential digestion with neuraminidase and β-galactosidase

500 µl of the desalted YC05 retentate was adjusted to pH 5.0 with 29 µl of a 700 mM sodium acetate buffer and digested with 1 U neuraminidase (type X; Sigma) for 24 h at 37° C. After lyophilization in a "Speedvac", the residue was taken up in 500 µl 50 mM Tris/HCl buffer, pH 7.3 and admixed with magnesium chloride (10 mM final concentration). 250 µl of this was withdrawn for gel electrophoretic analysis and the proliferation test, the remainder was incubated for 18 h at 37° C. with 10 U β-galactosidase (Sigma). After lyophilization it was taken up in 250 µl distilled water and the sample was examined in the proliferation test.

Incubation with glycopeptidase F

20 µl of a YC05 retentate was dried in a "Speedvac", subsequently taken up in the same volume of digestion buffer (20 mM potassium phosphate pH 6.8; 10 mM EDTA, pH 8; 0.2% Triton X 114; 0.1% SDS and 1% mercaptoethanol). 3 µl of a glycopeptidase F solution (glycopeptide-N-glycosidase; Boehringer Mannheim) was pipetted into this mixture and it was incubated overnight at 37° C. The digestion was stopped by addition of SDS sample buffer and analysed using SDS PAGE.

Detection of sugar components by use of the "Glycan detection kit"

The glycan detection kit sold by the Boehringer Company (Mannheim), which enables the detection of up to 1 ng glycoprotein, was used as an alternative test system for the detection of N- or O-glycosidically-linked glycan residues in the EMBIN I molecule.

10 and 20 µl of an EMBIN I sample purified by RP-HPLC was used for the derivatization and immunoblot test according to the manufacturer's instructions; 10 µg transferrin were used likewise as a control protein. The separation of the digoxigenin derivatives was carried out in a 1.5% SDS gel according to the Laemmli method. Transfer onto nitrocellulose (0.45 µm; Schleicher and Schuell) was carried out according to the method of Bjerrum et al. (in: Electrophoresis, p 315 ff (1986), Weinhein, "Verlag Chemie"). The part of the SDS gel in which the marker proteins and the untreated EMBIN I sample had been separated was stained with silver.

Phenol extraction 1 ml of a fraction with inhibitory activity after chromatography on hydroxylapatite was admixed with the same volume of a phenol solution which had been saturated with water and adjusted to pH 7.5 with Tris/HCl buffer, thoroughly mixed and briefly centrifuged in order to completely separate the phases. The aqueous phase was subsequently shaken out with the same volume of chloroform in order to remove residual phenol and again briefly centrifuged to separate the phases. All three phases (water, phenol, chloroform) were dried in a "Speedvac" and each was taken up in 1 ml 20 mM MOPS buffer pH 6.8 for the BAEC test.

Lipid extraction

20 µl of a fraction with inhibitory activity after gel filtration on BioGel P2 was admixed with a mixture of 50 µl methanol and 25 µl chloroform, thoroughly mixed and extracted overnight at 4° C. On the next day 40 µl of a water/chloroform mixture (1:1, v:v) was added to initiate phase separation. After a short centrifugation, both phases were separated, rotated to dryness in a "Speedvac" and taken up in the initial volume for gel electrophoresis.

Inactivation by diethylpyrocarbonate

100 µl of the diafiltered YC05 retentate was admixed with 1 µl diethylpyrocarbonate (Sigma), thoroughly mixed and incubated overnight at room temperature. The solution was dried in a vacuum concentrator and the residue was taken up in the original volume of distilled water. An insoluble precipitate was removed by centrifugation. The supernatant of the centrifugation was sterilized by filtration and tested in the proliferation test.

100 μl PBS was treated in the same way as a control mixture and also tested on the BAE cells.

Amino acid analysis of EMBIN I

Analysis of the amino acid composition was carried out according to the method described by Knecht and Chang with some modifications by a precolumn derivatization of the amino acids in the hydrolysate with 4-dimethylaminoazobenzene- 4'-sulfonyl chloride (dabsyl chloride) (Chang et al., Biochem. J. 199 (1981), 547–555; Knecht and Chang, Anal. Chem. 58 (1986), 2375–2379).

Dabsyl chloride from the Pierce Co. was dissolved at a concentration of 1.3 mg/ml in acetonitrile, aliquoted and stored at –20° C. During this process part of the dabsyl chloride dissolved at room temperature crystallizes out, and this can be brought back into solution by careful heating shortly before use.

Hydrolysis

For this 40 μl of each of the samples to be determined was pipetted in each case into a glass ampoule from the Wheaton Co. (Wheaton, Millville, N.J.) which had been thoroughly heated and had a capacity of 2 ml and they were dried in a vacuum concentrator.

After addition of 200 μl 6N HCl (Sigma; constant boiling) into each ampoule, these were closed hermetically in a water jet vacuum. The samples were hydrolysed in an oil bath at 110° C. They were usually hydrolysed for 24–60 hours. In order to take into account losses of individual amino acids which are partially destroyed during hydrolysis, 5 μl of a standardized amino acid mixture (Sigma) was hydrolysed and derivatised under the same conditions in each experiment.

Derivatization

After cooling the hydrolysates were transferred into 1.5 ml Eppendorf tubes and dried in a vacuum concentrator. The residues were taken up in 100 μl 0.1M sodium hydrogencarbonate buffer pH 8.3. 250 μl of the dabsyl chloride solution was then pipetted into each derivatization mixture, whereupon a light red precipitate appeared. In the subsequent heating to 70° C. in a water bath (12 min) this precipitate goes back into solution and a colour transition from light red via orange to yellow is observed. Following this actual coupling reaction, after which the amino acids are present in the hydrolysates as chromogenic derivatives, the samples were cooled to room temperature and subsequently adjusted to a final volume of 1 ml by addition of 650 μl 50 mM potassium phosphate/ethanol buffer pH 7.0 (1:1, v:v). Small flocculent precipitates which were present in individual samples were removed by a 5 minute centrifugation in a Beckmann bench centrifuge.

HPLC analysis of the amino acid derivatives

The chromatographic separation of the derivatized amino acids was carried out on a HPLC apparatus from the Kontron Company with 2 HPLC pumps of the 420 type, a 430 detector and the data processing system 450. The amino acid derivatives were detected at 436 nm. The volume of the installed sample loop was 75 μl. A C18 Ultrasphere ODS column (4.6×250 mm or 4.6×150 mm) from the Beckmann Co. that is packed with 5μ particles was used as the separation column.

The mobile phases A and B were composed according to the working instructions from the Beckmann Co. for their "Dabs-amino acid kit". Starting with a citric acid stock solution of 1 mol/l, a 0.1M stock solution was prepared first, the pH was adjusted to 6.5 with 5N NaOH.

The buffers were prepared as follows:

A: 150 ml 0.1M sodium citrate pH 6.5 40 ml dimethylformamide (DMF) 810 H₂O

B: 700 ml of a 4% solution of DMF in acetonitrile was added slowly to 300 ml of buffer A while stirring continuously.

The amino acids were separated by eluting the separation column with a multilinear gradient at a flow rate of 1.4 ml/min:

| Minutes | Duration | % A | % B |
|---------|----------|-----|-----|
| start | — | 71 | 29 |
| 2 | 14 | 49 | 51 |
| 16 | 5 | 14 | 86 |
| 21 | 1 | 0 | 100 |
| 22 | 5 | 0 | 100 |
| 27 | — | 71 | 29 |
| 30 | end of the chromatogram | | |

10 μl of each of the samples to be analyzed was used. The quantitative evaluation was carried out automatically by the data system 450 after calibration with the same volume of the amino acid standard.

The result of the amino acid analysis of the EMBIN I sample was compared with that of a control sample which only contained the buffer used for the RP-HPLC (5 mM heptanesulfonic acid; 0.04% TFA). This control sample was intended to show an eventual contamination of the mobile buffer with amino acids.

| Amino acid | Retention time (min) | Amount (pmol) | Difference from control (pmol) |
|---|---|---|---|
| ASX | 5.15 | 2.45 | 2.45 |
| GLX | 5.84 | 5.30 | 5.30 |
| SER | 10.32 | 1.40 | — |
| THR | 10.78 | — | — |
| ARG | 11.14 | — | — |
| GLY | 11.49 | — | — |
| ALA | 11.38 | — | — |
| PRO | 12.69 | 2.06 | 2.06 |
| VAL | 13.32 | 2.40 | 0.84 |
| MET | 14.86 | — | — |
| ILE | 15.13 | — | — |
| LEU | 15.61 | 3.18 | 3.18 |
| PHE | 17.10 | — | — |
| CYS-CYS | 18.79 | — | — |
| LYS | 21.13 | 2.87 | 1.41 |
| HIS | 21.35 | 2.68 | 2.68 |
| TYR | 22.31 | — | — |

The amounts of amino acids found are at the detection limit for this method. For example the characteristic peaks for serine, threonine, arginine, glycine and alanine are present in the chromatogram as are the peaks for isoleucine, phenylalanine and tyrosine. Nevertheless they were not identified by the integrator for the above-mentioned reason. Moreover the available chromatograms gave no indication for the occurrence of rarer amino acids.

We claim:

1. A process for isolating a compound that inhibits the proliferation of endothelial cells, comprising the steps of:

(a) homogenizing chicken embryo tissue or adult bovine brain tissue to produce a homogenate;

(b) centrifuging the homogenate;

(c) applying the homogenate to a cation exchanger and fractionating the substances which bind to the cation exchanger;

(d) separating any active fractions from step (c) by gel filtration chromatography; and (e) purifying any active fractions from step (d) by reverse phase HPLC under alkaline conditions or in the presence of an ion pair former;

wherein said compound has a molecular weight in the range of 2.5 to 6.2 kDa or 16 to 20 kDa as determined by SDS polyacrylamide gel electrophoresis and wherein said compound retains activity after heating for 60 minutes at 90° C., is resistant to nucleases and proteases and does not contain any detectable sugar or lipid parts.

2. The process of claim 1, further comprising applying the active fractions to a hydroxylapatite column after fractionation over the cation exchanger, and subjecting any eluant from the hydroxylapatite column to ultrafiltration.

3. The process of claim 2, wherein a membrane with a separation limit of 500 Da is used for the ultrafiltration.

4. The process of claim 1, wherein said gel filtration chromatography is carried out with a material which has a nominal exclusion limit of about 1 to 2 kDa.

5. The process of claim 1, wherein the reverse phase HPLC purification is carried out at an alkaline pH value greater than 8.

6. The process of claim 5, wherein the reverse phase HPLC purification is carried out at a pH value between 10 and 13.5.

7. The process of claim 1, wherein the reverse phase HPLC purification is carried out in the presence of an acidic ion pair former.

8. The process of claim 7, wherein the reverse phase HPLC purification is carried out in the presence of 0.1 to 50 mmol/l of an alkyl or arylsulfonic acid.

9. A compound which inhibits the proliferation of endothelial cells, wherein said compound is obtained by the following steps:

(a) homogenizing chicken embryo tissue or adult bovine brain tissue to produce a homogenate, (b) centrifuging the homogenate, (c) applying the homogenate to a cation exchanger and fractionating the substances which bind to the cation exchanger, (d) separating any active fractions from step (c) by gel filtration chromatography and (e) purifying any active fractions from step (d) by reverse phase HPLC under alkaline conditions or in the presence of an ion pair former;

wherein said compound has a molecular weight in the range of 2.5 to 6.2 kDa or 16 to 20 kDa as determined by SDS polyacrylamide gel electrophoresis and wherein said compound retains activity after heating for 60 minutes at 90° C., is resistant to nucleases and proteases and does not contain any detectable sugar or lipid parts.

10. The compound of claim 9, wherein said compound is inhibited by the addition of diethylpyrocarbonate.

11. A pharmaceutical composition useful for inhibiting the proliferation of endothelial cells, comprising a compound of claim 9 in combination with a pharmaceutically acceptable carrier.

12. A method for inhibiting the proliferation of endothelial cells comprising administering to a patient in need of such treatment, an effective amount of a compound obtained by the following process:

(a) homogenizing chicken embryo tissue or adult bovine brain tissue to produce a homogenate, (b) centrifuging the homogenate, (c) applying the homogenate to a cation exchanger and fractionating the substances which bind to the cation exchanger, (d) separating any active fractions from step (c) by gel filtration chromatography and (e) purifying any active fractions from step (d) by reverse phase HPLC under alkaline conditions or in the presence of an ion pair former;

wherein said compound has a molecular weight in the range of 2.5 to 6.2 kDa or 16 to 20 kDa as determined by SDS polyacrylamide gel electrophoresis and wherein said compound retains activity after heating for 60 minutes at 90° C., is resistant to nucleases and proteases and does not contain any detectable sugar or lipid parts.

13. The method of claim 12 wherein said compound inhibits capillary growth.

14. The method of claim 12 wherein said compound regulates the regeneration of blood vessels.

* * * * *